US011351362B2

(12) United States Patent
Månsson et al.

(10) Patent No.: US 11,351,362 B2
(45) Date of Patent: Jun. 7, 2022

(54) KIT AND SYSTEM FOR TRANSCRANIAL BRAIN STIMULATION

(71) Applicant: FLOW NEUROSCIENCE AB, Malmö (SE)

(72) Inventors: Daniel Månsson, Simrishamn (SE); Erik Rehn, Enebyberg (SE)

(73) Assignee: FLOW NEUROSCIENCE AB, Malmö (SE)

( * ) Notice: Subject to any disclaimer, the term of this patent is extended or adjusted under 35 U.S.C. 154(b) by 46 days.

(21) Appl. No.: 16/480,679

(22) PCT Filed: Feb. 1, 2018

(86) PCT No.: PCT/EP2018/052481
§ 371 (c)(1),
(2) Date: Jul. 25, 2019

(87) PCT Pub. No.: WO2018/141830
PCT Pub. Date: Aug. 9, 2018

(65) Prior Publication Data
US 2021/0128905 A1    May 6, 2021

(30) Foreign Application Priority Data

Feb. 2, 2017  (WO) ............... PCT/EP2017/052251

(51) Int. Cl.
*A61N 1/04* (2006.01)
*A61N 1/36* (2006.01)
*A61N 1/20* (2006.01)

(52) U.S. Cl.
CPC ......... *A61N 1/0456* (2013.01); *A61N 1/0484* (2013.01); *A61N 1/3603* (2017.08); *A61N 1/36025* (2013.01); *A61N 1/20* (2013.01)

(58) Field of Classification Search
CPC .. A61N 1/0456; A61N 1/3603; A61N 1/0484; A61N 1/20
See application file for complete search history.

(56) References Cited

U.S. PATENT DOCUMENTS 9,782,602 B1 * 10/2017 Lowin .................... G01K 13/00
10,327,984 B2 * 6/2019 Goodall ................. A61N 2/002
(Continued)

FOREIGN PATENT DOCUMENTS

WO    2009/137683 A2    11/2009
WO    WO-2014082064 A1 *  5/2014  ........... A61N 1/0456
(Continued)

OTHER PUBLICATIONS

International Search Report and Written Opinion dated May 22, 2018 for PCT/EP2018/052481 filed on Feb. 1, 2018, 9 pages.

*Primary Examiner* — Christopher A Flory
(74) *Attorney, Agent, or Firm* — Xsensus LLP

(57) ABSTRACT

A kit for transcranial brain stimulation is disclosed. The kit comprises a headset for transcranial brain stimulation, and a non-transitory computer-readable recording medium having recorded thereon a program which is executable on an electronic device having processing capabilities. The program comprises program code portions which when executed on the electronic device is configured to: store, in a computer memory, a schedule for performing the transcranial brain stimulation; and generate a control signal for the headset such that transcranial brain stimulation is performed according to the schedule for performing the transcranial brain stimulation. The headset comprises: a wireless transceiver configured to wirelessly communicate with the electronic device; a circuit comprising a first electrode, a second electrode and a power source configured to provide power to (Continued)

the circuit; and a controller being configured to control powering of the circuit according to the control signal.

4 Claims, 3 Drawing Sheets

(56) References Cited

U.S. PATENT DOCUMENTS

| | | | | |
|---|---|---|---|---|
| 11,000,669 | B2* | 5/2021 | Derungs | G06F 3/165 |
| 2010/0057159 | A1* | 3/2010 | Lozano | A61N 1/36096 |
| | | | | 607/45 |
| 2014/0350431 | A1 | 11/2014 | Hagedorn | |
| 2015/0005840 | A1* | 1/2015 | Pal | A61N 1/0476 |
| | | | | 607/45 |
| 2015/0119689 | A1* | 4/2015 | Pascual-Leone | A61N 2/006 |
| | | | | 600/407 |
| 2015/0238762 | A1* | 8/2015 | Pal | A61N 1/36034 |
| | | | | 607/45 |
| 2015/0335875 | A1* | 11/2015 | Goldwasser | A61N 1/36025 |
| | | | | 607/45 |
| 2015/0335888 | A1* | 11/2015 | Demers | A61N 1/36025 |
| | | | | 607/45 |
| 2015/0351655 | A1* | 12/2015 | Coleman | G16H 50/20 |
| | | | | 600/301 |
| 2016/0008620 | A1* | 1/2016 | Stubbeman | A61B 5/4848 |
| | | | | 607/45 |
| 2016/0008632 | A1* | 1/2016 | Wetmore | A61N 1/37247 |
| | | | | 601/2 |
| 2016/0074657 | A1 | 3/2016 | Kwan et al. | |
| 2016/0175589 | A1* | 6/2016 | Wingeier | A61B 5/4076 |
| | | | | 607/45 |
| 2016/0317809 | A1* | 11/2016 | Pal | A61N 1/36025 |
| 2017/0056642 | A1* | 3/2017 | Moffitt | G16H 50/20 |
| 2017/0080234 | A1* | 3/2017 | Gillespie | A61N 1/36025 |
| 2017/0113057 | A1* | 4/2017 | Goodall | A61N 1/36031 |
| 2017/0224990 | A1* | 8/2017 | Goldwasser | A61N 1/0456 |
| 2017/0319852 | A1* | 11/2017 | Wingeier | A61N 1/0456 |
| 2017/0361094 | A1* | 12/2017 | Cartledge | A61N 1/0472 |
| 2018/0133431 | A1* | 5/2018 | Malchano | A61B 5/0036 |
| 2018/0133504 | A1* | 5/2018 | Malchano | G02C 11/10 |
| 2018/0236231 | A1* | 8/2018 | Wingeier | A61B 5/4836 |
| 2019/0046794 | A1* | 2/2019 | Goodall | A61N 1/0456 |
| 2019/0113757 | A1* | 4/2019 | Van Heugten | G06F 3/011 |
| 2019/0159715 | A1* | 5/2019 | Mishra Ramanathan | |
| | | | | A61B 5/055 |
| 2019/0224481 | A1* | 7/2019 | Wingeier | A61B 5/165 |
| 2019/0232054 | A1* | 8/2019 | Levenberg | A61N 1/0484 |
| 2020/0302825 | A1* | 9/2020 | Sachs | G09B 19/00 |
| 2021/0169417 | A1* | 6/2021 | Burton | A61B 5/02055 |

FOREIGN PATENT DOCUMENTS

| | | |
|---|---|---|
| WO | 2016/017954 A1 | 2/2016 |
| WO | 2016/042499 A1 | 3/2016 |

* cited by examiner

KIT AND SYSTEM FOR TRANSCRANIAL BRAIN STIMULATION

CROSS-REFERENCE TO RELATED APPLICATIONS

The present application is based on PCT filing PCT/EP2018/052481, filed Feb. 1, 2018, which claims priority to PCT filing PCT/EP2017/052251, filed Feb. 2, 2017, the entire contents of each are incorporated herein by reference.

TECHNICAL FIELD

The present invention relates to a kit and a system for transcranial brain stimulation.

BACKGROUND OF THE INVENTION

Transcranial brain stimulation is, e.g., used to help stroke recovery and patients with brain injuries and to treat depression. An example of transcranial brain stimulation is transcranial direct current stimulation, tDCS, which is a well-known technique for non-invasive neurostimulation of the brain. Transcranial brain stimulation uses external electrodes placed on the head of the patient, whereby the head of the patient together with the electrodes forms a closed circuit. A current, either direct or alternating, is applied to the circuit, which acts on the neurons of the brain. The placement of the electrodes can be done by a physician, but when transcranial brain stimulation is used to treat depression it should be performed so often that it is highly impractical for a physician to be present. The patient may be given the electrodes and instructions on how to place them, but this is of course error-prone. Another problem is patient compliance—the patient must apply the therapy often enough for it to have effect, but not too often as this may lead to unwanted side effects. The lack of presence of a physician when the therapy is self-performed also leads to a lack of patient feedback and monitoring.

SUMMARY OF THE INVENTION

In view of the above, an objective of the invention is to solve or at least reduce one or several of the drawbacks discussed above. Generally, the above objective is achieved by the attached independent patent claims.

According to a first aspect a kit for transcranial brain stimulation is provided. The kit comprises a headset for transcranial brain stimulation, and a non-transitory computer-readable recording medium having recorded thereon a program which is executable on an electronic device having processing capabilities. The program comprises program code portions which when executed on the electronic device is configured to: store, in a computer memory, a schedule for performing the transcranial brain stimulation; and generate a control signal for the headset such that transcranial brain stimulation is performed according to the schedule for performing the transcranial brain stimulation. The headset comprises: a wireless transceiver configured to wirelessly communicate with the electronic device; a circuit comprising a first electrode, a second electrode and a power source configured to provide power to the circuit; and a controller being configured to control powering of the circuit according to the control signal.

The computer memory, onto which the schedule for performing the transcranial brain stimulation is stored, may be a computer memory of the electronic device. The computer memory, onto which the schedule for performing the transcranial brain stimulation is stored, may be a computer memory of the headset. The computer memory, onto which the schedule for performing the transcranial brain stimulation is stored, may partly be a computer memory of the headset and partly a computer memory of the electronic device, hence, the schedule for performing the transcranial brain stimulation may be distributed over a plurality of computer memories at different devices.

The kit provides the possibility for a user to perform a transcranial brain stimulation therapeutic schedule themselves with the aid of an electronic device, limiting the need for visits to or by a physician. The headset does not need to be wired to any controller, improving portability of the headset and increasing user comfort and convenience.

The program may further comprise program code portions which when executed on the electronic device is configured to remind the user to use the headset according to the schedule for performing the transcranial brain stimulation. This provides a kit for performing transcranial brain stimulation where the user can be conveniently prompted to wear the headset and signaled when to remove it. This provides a safety measure against over-use of the headset by the user due to negligence or ignorance.

By scheduling the use of the headset for transcranial brain stimulation the usage may be limited according to the schedule. In this way over-use may be avoided. If the user tries to over-use the headset the kit may indicate this by issuing an error-message. The error message may be issued via a display of the electronic device. The schedule for performing the transcranial brain stimulation may comprise information pertaining to the frequency of usage of the headset for performing the transcranial brain stimulation. For example, one session per day, one session per every second day, X sessions per every week, etc.

The program may further comprise program code portions which when executed on the electronic device is configured to display information on a display of the electronic device in accordance with a schedule for displaying the information, wherein the schedule for displaying information is related to the schedule for performing the transcranial brain stimulation. This allow for setting up of a therapy program comprising both the actual transcranial brain stimulation but also to include viewing of videos and/or participation in cognitive games during or in between specific transcranial brain stimulation sessions. Hence, a kit providing enhanced treatment programs is provided.

The program may further comprise program code portions which when executed on the electronic device is configured to prompt the user to input information pertaining to status of the user. This provide the possibility for remote review of the status of the user. For example, the health of the user may be monitored in a continent manner without the need for a physician at the site of the user.

The program may further comprise program code portions which when executed on the electronic device is configured to update the schedule for performing the transcranial brain stimulation. This provide the possibility for remote update of the schedule for performing the transcranial brain stimulation. This further reduces the need for involvement of a physician at the site of the user upon performing the transcranial brain stimulation.

The program may further comprise program code portions which when executed on the electronic device is configured to store information pertaining to performed transcranial brain stimulation on a computer memory. The progress of the therapy program may hence be monitored. This provide the possibility for remote review of progress of the therapy program. This further reduces the need for involvement of a physician at site upon performing the transcranial brain stimulation. This further reduces the need for involvement of a physician at site upon performing the transcranial brain stimulation.

The electronic device may be a handheld electronic device.

The program may be an application downloadable to the electronic device via an application providing service.

According to a second aspect a system for transcranial brain stimulation is provided. The system comprises a server and a plurality of kits according to the first aspect.

The program may further comprise program code portions which when executed on an electronic device is configured to: establish a first communication channel between the electronic device on which the program is executed and the server; and establish a second communication channel between the electronic device on which the program is executed and the headset, wherein first and second communication channels are independent from each other.

The program may further comprise program code portions which when executed on an electronic device is configured to: prompt the user of the electronic device, on which the program is executed, to input information pertaining to status of the user; and send the information pertaining to status of the user to the server.

The program may further comprise program code portions which when executed on an electronic device is configured to: record information pertaining to performed transcranial brain stimulation; and send the recorded information pertaining to performed transcranial brain stimulation to the server.

The server may be configured to correlate and store the information pertaining to status of the user and the information pertaining to performed transcranial brain stimulation.

The program may further comprise program code portions which when executed on an electronic device is configured to: correlate the information pertaining to status of the user and the information pertaining to performed transcranial brain stimulation before being sent to the server.

The above mentioned features of the kit, when applicable, apply to this second aspect as well. In order to avoid undue repetition, reference is made to the above.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles "a," "an," "the," and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

BRIEF DESCRIPTION OF THE DRAWINGS

The above and other aspects of the present invention will now be described in more detail, with reference to appended drawings showing embodiments of the invention. The figures should not be considered limiting the invention to the specific embodiment; instead they are used for explaining and understanding the invention.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION OF THE INVENTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

Figure 1:
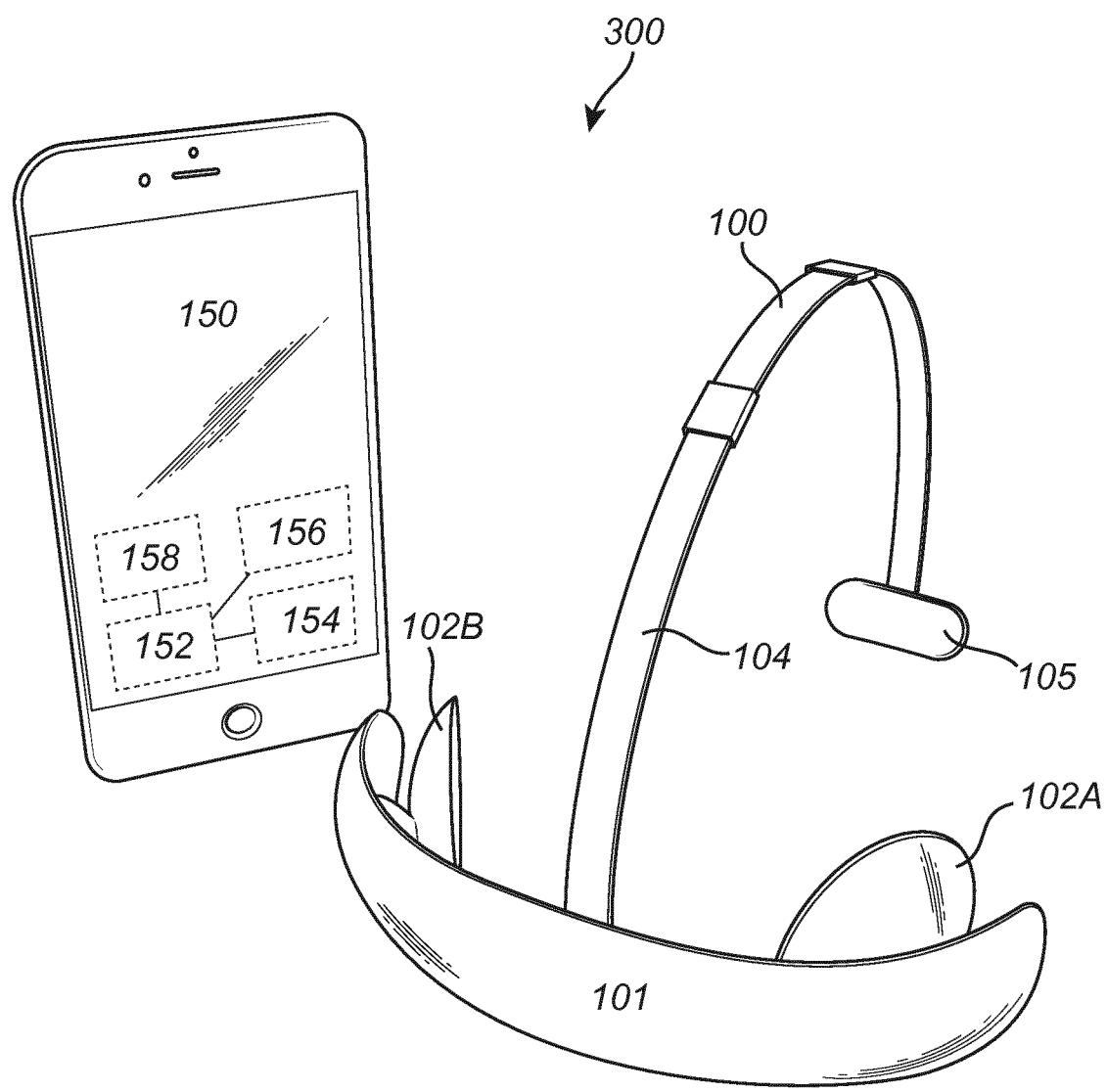
FIG. 1 illustrates a kit comprising a headset for transcranial brain stimulation and an electronic device configured to control the headset.

In FIG. 1, a kit 300 for transcranial brain stimulation is illustrated. The kit comprises a headset 100 for transcranial brain stimulation and a non-transitory computer-readable storage medium 154 having stored thereon a computer program being executable on a device having processing capabilities. The non-transitory computer-readable storage medium 154 is typically located in an electronic device 150. The non-transitory computer-readable storage medium 154 will in this context also be referred to as a memory of the electronic device 150. The memory 154 may be any type of non-transitory computer-readable storage medium which may persistently store digital information. The memory 154 may, e.g., be a solid state drive, a flash memory or any other device which may persistently store digital information. The electronic device 150 comprises a processor 152 and the non-transitory computer-readable storage medium 154. The electronic device may e.g. be a handheld electronic device, such as a laptop, a smartphone, a tablet or a smartwatch. The processor 152 is configured to execute computer programs stored on the non-transitory computer-readable storage medium 154. Hence, the non-transitory computer-readable storage medium 154 having recorded thereon a computer program which is executable by the processor 152 of the electronic device 150. The electronic device 150 may further comprise a wireless transceiver 156. The wireless transceiver 156 is configured to establish a communication channel with the headset 100. The wireless transceiver 156 may be configured to wirelessly communicate with the headset 100. Any suitable wireless protocol, such as Bluetooth®, Wi-Fi, ZigBee®, or wireless USB, may be used. The electronic device 150 may further comprise a network communication unit 158. The network communication unit 158 is configured to establish a communication channel with a server via a computer network. The network communication unit 158 is preferably configured to communicate wirelessly with the server. Any suitable wireless protocol, such as 3G, 4G, 5G, or Wi-Fi, may be used. The communication between the electronic device 150 and the server and the communication between the electronic device 150 and the headset 100 is preferably independent of each other.

The computer program may be an application downloadable to the electronic device 150 via an application providing service. The computer program comprises code portions which when executed on the electronic device 150 is configured to perform different acts.

A code portion of the computer program is configured to store a schedule for performing a transcranial brain stimulation in a computer memory. The schedule for performing transcranial brain stimulation may comprise information pertaining to how often and/or when the headset is to be used for performing a session of the transcranial brain stimulation. This information may e.g. be indicative of a time window within a session of the transcranial brain stimulation is to be performed. The time window may e.g. be defined with a specific day or with some specific days. For example, this information may be indicative of that the session shall be performed between certain hours of a day, that the session shall be performed every second day, etc. The user may also be prompted to schedule the next session. Within the limits of the overall schedule. For instance, the user may be prompted to plan when he/she will do the next session. This may comprise information on time and/or day for the next session. This information may then be put into the schedule for performing a transcranial brain stimulation. Hence, the schedule may be updated. The user may then be reminded so that the next session is performed at the next scheduled session. In this way the user may influence the schedule.

The schedule for performing transcranial brain stimulation may further comprise information pertaining to how a specific session shall be composed. This information may e.g. be indicative of currents to be used for a specific stimulus within the specific session, intervals between stimuli of the specific session, duration of a stimulus of the specific session, duration of the specific session, etc. The schedule for performing transcranial brain stimulation may moreover comprise information pertaining to displaying of video sequence to be watched in connection with receiving the transcranial brain stimulation, see below for more details. This information may e.g. be indicative of which video sequence to be displayed and how often. The schedule for performing transcranial brain stimulation may furthermore comprise information pertaining to execution of cognitive games to be played in connection with receiving the transcranial brain stimulation. This information may e.g. be indicative of which games to be executed and how often. The schedule for performing transcranial brain stimulation may further comprise information pertaining to prompting the user to input information pertaining to status of the user. This information may e.g. be indicative of how often information pertaining to status of the user shall be prompted for.

The computer memory onto which the schedule for performing the transcranial brain stimulation is stored may be a memory of the electronic device 150, for example, the non-transitory computer-readable storage medium 154. Alternatively, the computer memory may be a memory of the headset 100. Yet alternatively, the computer memory may be a memory of the server. Yet alternatively, the schedule for performing the transcranial brain stimulation may be stored at a plurality of the above mentioned computer memories. Further, alternatively, the schedule for performing the transcranial brain stimulation may be stored distributed on a plurality of the above mentioned computer memories. Hence, different portions of the schedule may be stored on different memories, the storing of the schedule may be distributed over a plurality of memories. For example, the information pertaining to how often and/or when the headset is to be used for performing a session of the transcranial brain stimulation may be stored on the memory of the electronic device and the information pertaining to how a specific session shall be composed may be stored on the memory of the headset. The full schedule for performing the transcranial brain stimulation may be stored on the server.

A code portion of the computer program may be configured to generate a control signal for the headset 100. The control signal comprising information pertain to how to control the headset 100 such that transcranial brain stimulation is performed according to the schedule for performing the transcranial brain stimulation. The control signal may be seen as a, from the schedule, generated control signal, wherein the control signal is generated at the electronic device 150. This at the electronic device 150 generated control signal may then be sent from the electronic device 150 to the headset 100. A controller 210 of the headset may then be configured to control a transcranial brain stimulation according to the received control signal. Alternatively, or in combination, the control signal may be seen as an extraction of a portion of the schedule for performing the transcranial brain stimulation, wherein the portion comprises information pertain to how to control the headset 100 such that transcranial brain stimulation is performed. The portion of the schedule may then be sent from the electronic device 150 to the headset 100. The controller 210 of the headset may then be configured to control a transcranial brain stimulation according to the received portion of the schedule.

A code portion of the computer program may be configured to prompt a user of the electronic device to identify herself. By this it may be safeguarded that the headset for transcranial brain stimulation may only be used by users intended to use it.

A code portion of the computer program may further be configured to remind the user to use the headset according to the schedule for performing the transcranial brain stimulation. Reminding the user when the user shall use the headset 100 counteracts negligence or unwitting non-compliance, e.g. due to misunderstanding or miscommunication, in relation to the therapy on account of the patient. The reminder may be prompted to the user using one or more of a loudspeaker of the electronic device 150, a light source of the electronic device 150, a vibrator of the electronic device 150 and a display of the electronic device 150. For example, the user may be prompted by a message displayed on the display of the electronic device 150. Alternatively, or in combination, the reminder may be prompted to the user using one or more of a loudspeaker 216, a light source 218, and a vibrator 220 of the headset 100. The loudspeaker 216, the light source 218, and the vibrator 220 of the headset 100 will be discussed in more detail below.

A code portion of the computer program may further be configured to display information on the display of the electronic device in accordance with a schedule for displaying information. The schedule for displaying information may relate to the schedule for performing the transcranial brain stimulation. The displayed information may e.g. be a video sequence to be watched in connection with receiving the transcranial brain stimulation. The video sequence may be video lesson being part of a treatment program. The video sequence may be an instructions video instructing the user how to put on and use the headset 100.

A code portion of the computer program may further be configured to execute cognitive games. The user of the kit 300 may for example be prompted to play a cognitive game during the transcranial brain stimulation.

A code portion of the computer program may further be configured to prompt the user to input information pertaining to status of the user. The user may be prompted by displaying a message on the display of the electronic device 150. The input information prompted for may be information pertaining to information about the user's current health. For example, information according to Phq-9, Hamilton Rating Scale for Depression (HRSD), Beck Depression Inventory (BDI, BDI-1A, BDI-II), Montgomery Åsberg Depression Rating Scale (MADRS, MADRS-s), Young Mania Rating Scale (YMRS) or any other psychiatric rating scale may be prompted for. The input information prompted for may further be one or more of information pertaining to age of the user, sex of the user, intake of pharmaceuticals of the user, training habits of the user, eating habits of the user, sleeping habits of the user, the geographical location of the user, the user's relationship to their surrounding family/friends and working situation of the user.

The user may input such information through input means of the electronic device. An example of an input means is a keyboard (virtual on a touch screen or realized as mechanical buttons). The input information pertaining to status of the user may then be stored in the computer memory. The computer memory used for storing the input information pertaining to status of the user may be the memory of the server. The input information pertaining to status of the user may then be provided to a physician for reviewing the schedule for the transcranial brain stimulation of the user.

A code portion of the computer program may further be configured to store information pertaining to performed transcranial brain stimulation in a computer memory. The computer memory may be the computer memory of the server. The information pertaining to performed transcranial brain stimulation may then be provided to a physician for reviewing the schedule for the transcranial brain stimulation of the user of the kit 300. Hence, means for monitoring the patient's progress through the therapy is provided. This further reduces the need for involvement of a physician upon performing the transcranial brain stimulation.

By being provided with the input information pertaining to status of the user and the information pertaining to performed transcranial brain stimulation the physician is provided with the possibility to assess the progress of the user and to make any adjustments required to the user's schedule for transcranial brain stimulation as well as inform the user that such adjustments have been made.

A code portion of the computer program may further be configured to update the schedule for performing the transcranial brain stimulation. This gives the possibility, for e.g. the physician, to adjust the schedule for transcranial brain stimulation.

Figure 3:
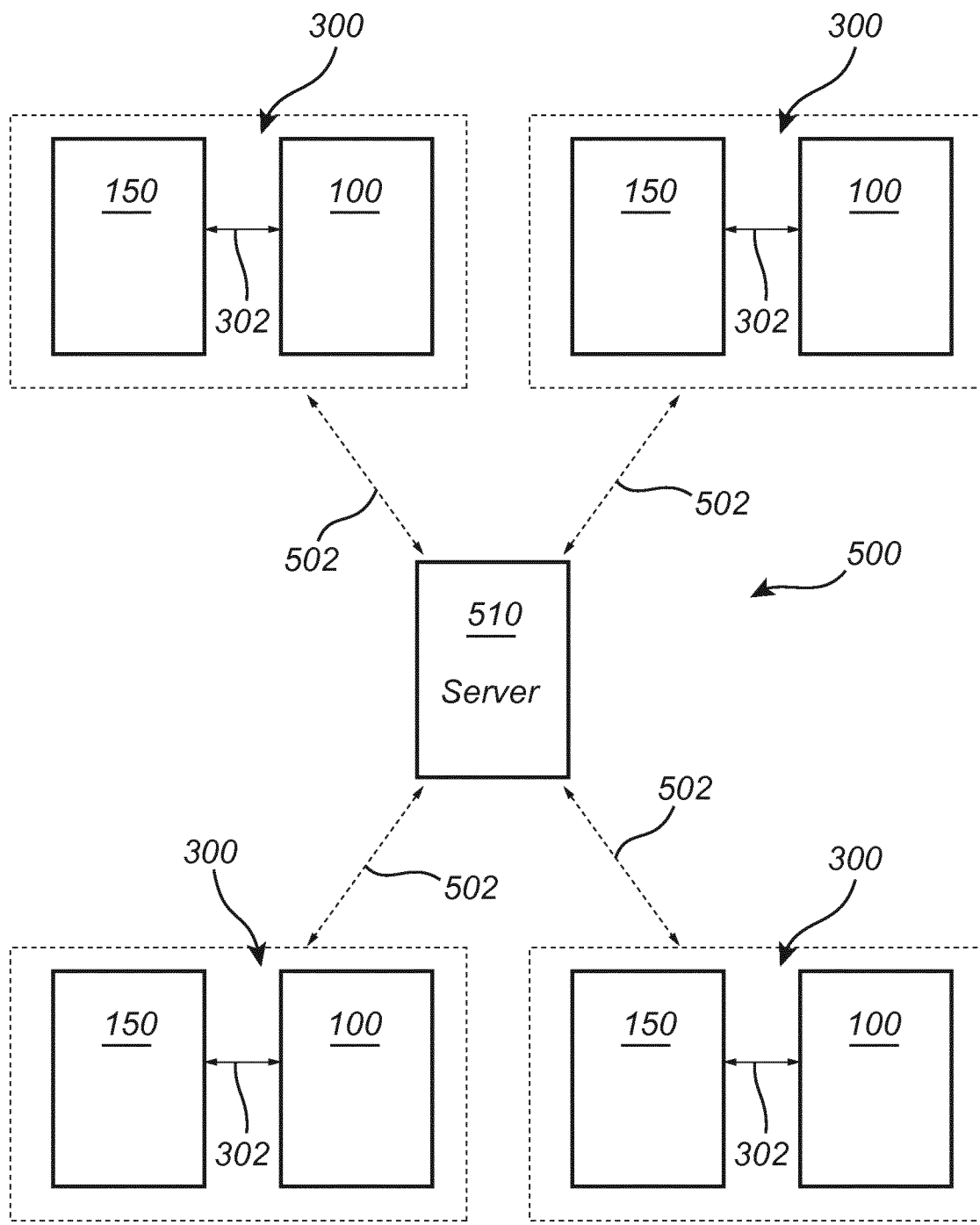
FIG. 3 illustrates a system for transcranial brain stimulation comprising a plurality of kits and a server.

FIG. 3 illustrates a system 500 comprising a server 510 and a plurality of kits 300. The server 510 is configured to individually communicate with the each of the plurality of kits 300. The communication is realized by establishing communication channels 502 over a computer network or cellular network. As mentioned above the communication channels 502 between the server 510 and an electronic device 150 of a kit 300 is independent from a communication channel 302 between the electronic device 150 of a kit 300 and a headset 100 of the kit 300. The server 510 is configured to communicate with the electronic devices 150 in each of the plurality of kits 300. Such a system 500 facilitates centralized planning of schedules for transcranial brain stimulation. Such a system 500 also facilitates centralized evaluation of the performed treatment program comprising the transcranial brain stimulation and possibly also watching of video lessons, playing of cognitive games, etc. Hence, the system 500 facilitates usage of the kit 300 for transcranial brain stimulation in a home environment with reduced need of in person consultation with a physician.

Further, the input information pertaining to status of the user may be correlated with the information pertaining to performed transcranial brain stimulation. Such correlated information may be stored at the server 510. The correlation may be made by program code portions at the different electronic devices 150 or at the server 510. Further, such correlated information may be used for training e.g. an artificial neural network to determine a schedule for performing transcranial brain stimulation based on information pertaining to status of a user a kit 300 for transcranial brain stimulation. For the transcranial brain stimulation to be as effective as possible the transcranial brain stimulation (and possibly also thereto associated cognitive games and/or video lessons, scheduling and motivational functions being part of a treatment program) is to be adapted to the individual user. Different users respond differently to the amount and order of brain stimulation, video lessons and/or cognitive games. Therefore, the transcranial brain stimulation, the video lessons and/or cognitive games is to be optimally controlled per user. A decision engine may be used for performing this control. The decision engine may comprise both hard-coded rules and learned rules. An example of such a decision engine is an engine based on reinforcement learning. The decision engine may use individual traits and/or treatment history as input for determining a schedule for transcranial brain stimulation. As mentioned above the input/output mapping of the decision engine may partly be based on hardcoded rules and partly on learned rules. The hardcoded rules may be derived from domain knowledge, for example in what order videos should be presented and how often the user shall be prompted to input information pertaining to status of the user. The learned rules may be derived using machine learning, for example based on reinforcement learning, supervised learning or unsupervised learning. The learning part may, as mentioned above, be based on an artificial intelligence paradigm called reinforcement learning with the goal to detect nonobvious decision rules from large quantities of user data. Reinforcement learning deals with problems where the outcome of a sequence of actions is delayed, which is what we have in our case. The actions of the decision engine are recommendations to the user, and the outcome we want to optimize for may be a subjective self-rating score of the user at the end of a treatment program comprising the transcranial brain stimulation. Important to note here is that we can't measure how good each recommendation is in itself, but instead only get to know the end outcome of a long sequence of recommendations. Reinforcement learning is a collection of methods to optimize these kind of decision sequences, by penalizing bad decisions and promoting good decisions based on an end outcome.

Figure 2:
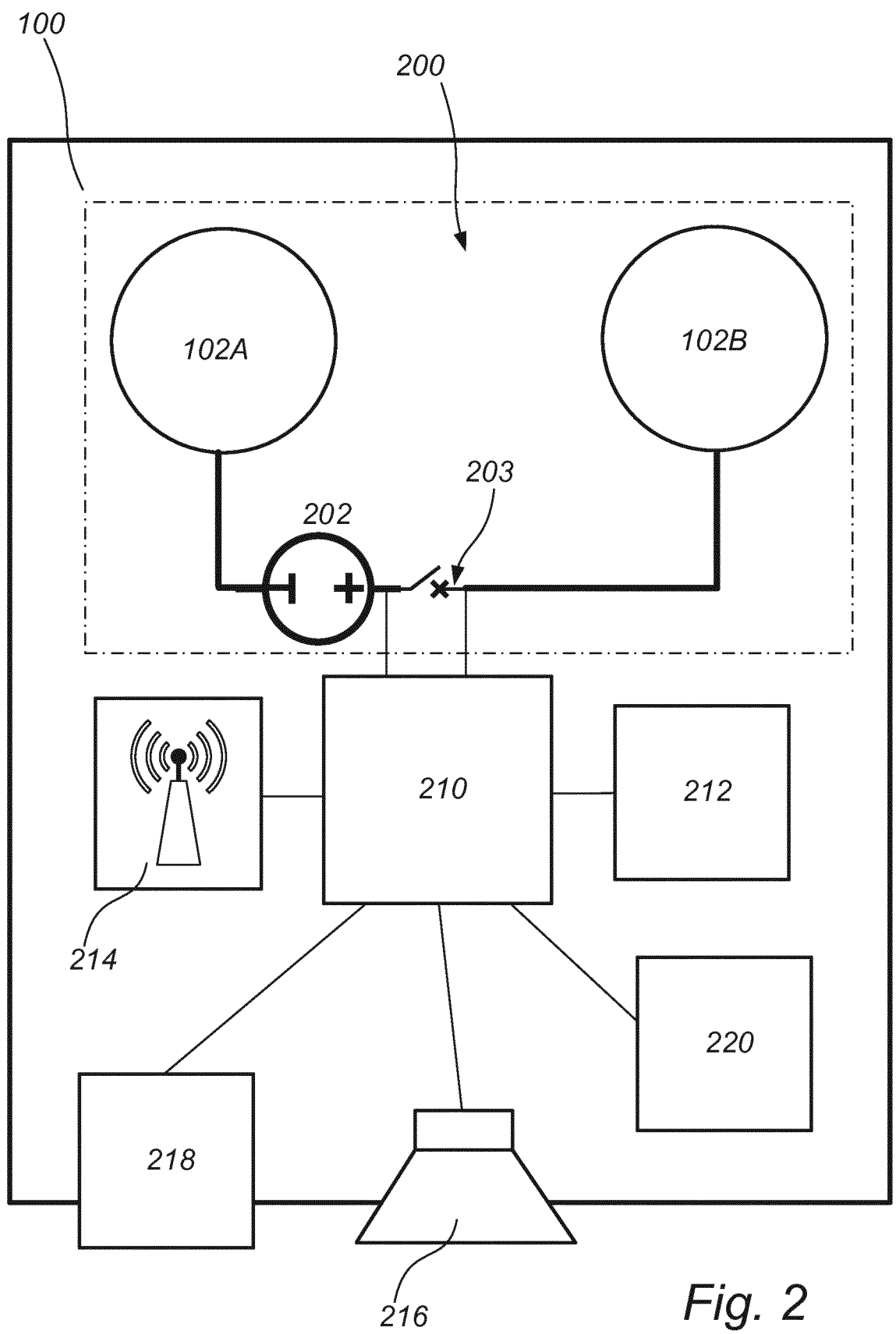
FIG. 2 is a schematic sketch of a headset for transcranial brain stimulation.

In connection with FIG. 2 the headset will be discussed in more detail. The headset comprises first and second electrodes 102A, 102B. The first and second electrodes 102A, 102B are comprised in a circuit 200. The circuit 200 is configured to be powered according to a schedule for performing transcranial brain stimulation. The first and second electrodes 102A, 102B are connected in the circuit 200. The circuit 200 further comprises a power source 202 and a switch 203. Upon the headset 100 being worn by the user and upon the switch 203 is engaged, a closed circuit comprising the first and second electrodes 102A, 1028, the user's forehead and the power source 202 is formed. This allows current to flow through the user's cranium. The power source 202 may be a battery. The battery may be a chargeable battery.

The headset 100 may further comprise a controller 210. The controller 210 is configured to periodically power the circuit 200 according to a schedule for performing transcranial brain stimulation. Thereby a current is periodically provided to user's brain for performing the transcranial brain stimulation. The controller 210 is configured to periodically control the switch 203. The controller 210 may be hardware or software implemented. The controller 210 may comprise a microcontroller, a system of microcontrollers, or any type of processor or control circuit which can engage and disengage the switch 203. This provides a headset 100 which may vary the electric impulses to the head of the user according to schemes for transcranial brain stimulation.

The headset 100 may further comprise a memory 212. The memory may be any type of non-volatile memory configured to store digital data. The memory 212 may, e.g., be a solid state drive, a flash memory or any other device which can persistently store digital information. The memory 212 may, e.g., be configured to store a schedule for performing the transcranial brain stimulation, or at least a portion of the schedule for performing the transcranial brain stimulation. Especially, the portion of the schedule for performing the transcranial brain stimulation comprising information pertaining to how a specific session shall be composed, this information may e.g. be indicative of currents to be used for a specific stimulus within the specific session, intervals between stimuli of the specific session, duration of a stimulus of the specific session, duration of the specific session, etc. Hence, the schedule for performing the transcranial brain stimulation may comprise information pertaining to when to open and close the switch 203. Further, the portion of the schedule for performing the transcranial brain stimulation stored on the memory 212 of the headset 100 may comprise information pertaining to when the user shall wear the headset 100 in order to receive the transcranial brain stimulation. The controller 210 may be arranged to read data from the memory 212. Hence, the controller 210 may be configured to receive information from the memory 212 on the schedule for performing the transcranial brain stimulation. However, it is realized that the schedule for transcranial brain stimulation, or at least portions of the schedule for transcranial brain stimulation, may be stored elsewhere in some other memory accessible by the controller 210. For example, the controller 210 may be arranged to receive data from other memories. The controller 210 may be arranged to receive data from the electronic device 150. The controller 210 may be arranged to receive data from the server 510. The controller 210 may further be configured to write data to the memory 212. Hence, the controller 210 may be configured to write data to the memory 212 pertaining to performed transcranial brain stimulation. Hence, means for monitoring the patient's progress through the therapy is provided. This further reduces the need for involvement of a physician upon performing the transcranial brain stimulation. The controller 210 may be configured to write data to the memory 154 of the electronic device 150. This may be made by sending the information to be stored at the electronic device 150, via a wireless transceiver 214 of the headset 100, to the electronic device 150. The wireless transceiver 214 is configured to wirelessly communicate with the electronic device 150. Any suitable wireless protocol, such as Bluetooth, Wi-Fi®, ZigBee®, or wireless USB, may be used. Hence, a wireless communication channel may be established between the wireless transceiver 214 of the headset 100 and the wireless transceiver 156 of the electronic device 150.

The wireless communication channel between the wireless transceiver 214 of the headset 100 and the wireless transceiver 156 of the electronic device 150 may further be used by the controller 210 of the headset 100 to receive data from the electronic device 150. For example, data stored on the memory 154 of the electronic device 150, e.g. data relating to the schedule for transcranial brain stimulation. Further, the wireless communication channel between the wireless transceiver 214 of the headset 100 and the wireless transceiver 156 of the electronic device 150 may be used by the controller 210 of the headset 100 to receive data routed by the electronic device 150. For example, data stored on the memory of the server 510 that are sent to the controller 210 via the electronic device 150. An example of data that may be routed by the electronic device 150 is data relating to the schedule for transcranial brain stimulation that are stored on the memory of the server 510. Moreover, the controller 210 may be configured to write data to the memory of the server 510. Even that kind of data may be routed via the electronic device 150. The data written to the memory of the server 510 may be data pertaining to performed transcranial brain stimulation.

As was briefly mentioned above, the headset 100 may further be configured to signal when the user shall wear or take off the headset 100 for receiving the transcranial brain stimulation. Signaling to the user when the user shall wear or take off the headset 100 counteracts negligence or unwitting non-compliance, e.g. due to misunderstanding or miscommunication, in relation to the therapy on account of the patient. The signaling can be done in many different ways. For this purpose, the headset 100 may comprise a speaker 216. The controller 210 may be configured to control the speaker 216. The speaker 216 is configured to emit sound pertaining to information reminding the user to wear or remove the headset 100. Some non-limiting examples of sounds are beeping sounds and voice synthesis. The loudspeaker 216 may be arranged in the forehead frame 101. The headset 100 may comprise a light source 218. The light source 218 may e.g. comprise one or more LEDs. The controller 210 may be configured to control the light source 218. The light source 218 is configured to emit light pertaining to information reminding the user to wear or remove the headset 100. For example, the light source 218 may be configured to emit light having different colors for reminding the user to wear or remove the headset 100. The light source 218 may be configured to emit light pulses of different frequency to remind the user. The light source 218 may be arranged in the forehead frame 101. The headset may comprise a vibrator 220. The controller 210 may be configured to control the vibrator 220. The vibrator 220 is configured to emit vibrate in order to remind the user to wear or remove the headset 100. The vibrator may be arranged in the forehead frame 101. Any combination of the loudspeaker 216, the light source 218 or the vibrator 220 may be used for reminding the user to wear or remove the headset 100. Hence, just one of them, two of them, or all of them may be used for reminding the user to wear or remove the headset 100.

The headset 100 may be designed any various ways. One example of a headset design is illustrated in FIG. 1. According to this exemplified design, the headset 100 comprises a forehead frame 101 and a bracket 104. The shape of the forehead frame 101 is designed to fit a forehead of a user of the headset 100. The forehead frame is designed as a single member. This member is shaped as an elongated arch. Hence, the forehead frame 101 is defining an elongated arch. This allows the forehead frame 101 to follow approximately the shape of the forehead of the user when placed on the head. The forehead frame 101 may be manufactured by e.g. plastic, composite materials, metal or any other suitable material.

The forehead frame 101 is configured to support the first and second electrodes 102A, 102B. The forehead frame 101 is configured to support the bracket 104. The first electrode 102A is arranged at a first end portion of the forehead frame 101. The second electrode 102B is arranged at a second end portion of the forehead frame 101. Hence, the first and second electrodes 102A, 102B are placed on the forehead frame 101 such that when the forehead frame 101 is worn by the user, the first and second electrodes 102A, 102B will come in contact with the forehead on either side of the user's head.

The bracket 44104 is arranged at a center portion of the forehead frame 101. The bracket 104 may be arranged to the forehead frame 101 in any suitable way. For example, the bracket 104 may be screwed, glued, or fastened in any other suitable way to the forehead frame 101. In this context the phrase "center portion" should be understood to refer to any part of the longitudinal extension of the forehead frame 101 which lies between the first and second electrodes 102A, 102B. The bracket 104 has a longitudinal extension which, when the headset 100 is used, extends from the forehead of the user towards the back of the user's head. In this way, the bracket 104 ensures that the user wears the headset 100 such that the first and second electrodes 102A, 102B come in contact only with their respective side of the user's forehead. The bracket 104 may be constructed such that its extension from the frame is variable, ensuring a better fit for the user. This can be achieved in many ways, which the skilled person understands. Alternatively, the bracket 104 may be of fixed length. The bracket 104 may further comprise a support cushion 105 arranged at an end portion of the bracket 104 being opposite to where the bracket 104 is arranged at the forehead frame 101. The cushion 105 makes the bracket 104 more comfortable for the user.

The in FIG. 1 illustrated exemplified headset 100 provides a headset for performing transcranial brain stimulation wherein the electrodes are unlikely to be placed incorrectly on the forehead of the user. This has the advantage of allowing for transcranial brain stimulation to be performed without a physician available to place the electrodes on the head of the patient. Furthermore, the headset may be designed to be lightweight and comfortable, eliminating the need for fabric headwear which may be warm and uncomfortable when worn for extended periods of time. This further provides a comfortable headset which is impossible to mount such that the direction of the current is reversed, which may be critical in for example transcranial direct current stimulation, tDCS. During electrical transcranial brain stimulation, the potential of neuronal cells is influenced by an applied electric field. This field influences the neuronal cells under the stimulated area and pushes them closer or further away from their activation threshold.

The first and second electrodes 102A, 102B may be configured to pivot to some degree. Thus, a headset 100 is provided where the major surface of each electrode 102A, 102B is pivoted to be principally parallel to the surface of the forehead of the user. The first and second electrodes 102A, 102B need not be configured to pivot. A more comfortable headset which is adaptable to many different shapes of patient foreheads and reduces the need for size adaptability of the headset is provided.

The first and second electrodes 102A, 102B may be of any type of conducting material suitable for repeated use. Alternatively, the first and second electrodes 102A, 102B may be configured for one-time use only, in which case they are to be replaced by the user between uses.

The first and second electrodes 102A, 102B may comprise an adhesive layer. The adhesive layer may be discarded after use. The adhesive layer ensures proper contact between the electrode and the forehead of the user while also providing a hygienic solution. For example, the adhesive layer may ensure that the headset 100 does not drift during use, securing it in place on the head of the patient.

The headset 100 may of course be provided with further electrodes, in case the desired scheme for transcranial brain stimulation so requires.

For some schemes of transcranial brain stimulation, the first and second electrodes 102A, 102B correspond to a first and second side of the user's forehead, respectively. By this is meant that each electrode 102A, 102B is configured to be brought into contact only with either the left or the right side of the user's forehead.

The illustrated example of a headset 100 in FIG. 1 is just one example of a headset 100 that may be used in the kit 300 or system 500 for transcranial brain stimulation disclosed herein. The headset 100 may be designed in many different alternative ways. According to one example, the headset 100 may not comprise the bracket 104 but only the forehead frame 101. According to another example, the headset 100 is a conventional fabric headwear.

The person skilled in the art realizes that the present invention by no means is limited to the preferred embodiments described above. On the contrary, many modifications and variations are possible within the scope of the appended claims.

As described above, the headset comprises a wireless transceiver. This provides the possibility for the headset to communicate wirelessly with the electronic device over a network protocol such as Bluetooth® or Wi-Fi. The skilled person understands that any network protocol capable of transmitting digitally represented data is possible to use.

The system may, through the electronic device, also provide the user with information about the transcranial brain stimulation progress such as logs of their use, changes to their schedule recommended by the physician, status of the headset regarding e.g. battery charge state or malfunctions, or any other information.

Further, the power source 202 of the headset 100 may be a chargeable battery. The headset may then comprise a charging port. The charging port may be located on an inside surface of the forehead frame 101. The inside surface of the forehead frame 101 being the surface of the forehead frame that is facing the forehead of the user upon use of the headset 100. This design will ensure that the headset cannot be charged upon usage of the same. This will enhance the safety of usage of the headset 100.

As shown through this description, a headset, a kit and a system for transcranial brain stimulation is provided which allows a user to autonomously and conveniently perform steps of such treatment which previously required visits to or by a physician.

Additionally, variations to the disclosed embodiments can be understood and effected by the skilled person in practicing the claimed invention, from a study of the drawings, the disclosure, and the appended claims.

The invention claimed is:

1. A system comprising a server and a plurality of kits, wherein each kit comprises a headset for transcranial brain stimulation, and a non-transitory computer-readable recording medium having recorded thereon a program which is executable on an electronic device having processing capabilities, wherein the program comprises program code portions which when executed on the electronic device is configured to:
- establish a first communication channel between the electronic device on which the program is executed and the server, and establish a second communication channel between the electronic device on which the program is executed and the headset, wherein first and second communication channels are independent from each other,
- store, in a computer memory, a schedule for performing the transcranial brain stimulation,
- generate a control signal for the headset such that transcranial brain stimulation is performed on a user according to the schedule for performing the transcranial brain stimulation,
- prompt the user of the electronic device on which the program is executed to input information pertaining to status of the user,
- send the information pertaining to status of the user to the server,
- record information pertaining to performed transcranial brain stimulation of the user, and
- send the recorded information pertaining to performed transcranial brain stimulation of the user to the server;

wherein the headset comprises:
- a wireless transceiver configured to wirelessly communicate with the electronic device,
- a circuit comprising a first electrode, a second electrode, and a power source configured to provide power to the circuit, and
- a controller being configured to control powering of the circuit according to the control signal;

wherein the server is configured to correlate and store the information pertaining to status of the user and the information pertaining to performed transcranial brain stimulation of the user.

2. The system according to claim 1, wherein prompt the user of the electronic device on which the program is executed to input information pertaining to status of the user comprises prompt the user of the kit to input information pertaining to status of the user according to Phq-9, Hamilton Rating Scale for Depression (HRSD), Beck Depression Inventory (BDI, BDI-1A, BDI-II), Montgomery Asberg Depression Rating Scale (MADRS, MADRS-s), Young Mania Rating Scale (YMRS) or any other psychiatric rating scale.

3. A system comprising a server and a plurality of kits, wherein each kit comprises a headset for transcranial brain stimulation, and a non-transitory computer-readable recording medium having recorded thereon a program which is executable on an electronic device having processing capabilities, wherein the program comprises program code portions which when executed on the electronic device is configured to:
- establish a first communication channel between the electronic device on which the program is executed and the server, and establish a second communication channel between the electronic device on which the program is executed and the headset, wherein first and second communication channels are independent from each other,
- store, in a computer memory, a schedule for performing the transcranial brain stimulation on a user,
- generate a control signal for the headset such that transcranial brain stimulation is performed on the user according to the schedule for performing the transcranial brain stimulation,
- prompt the user of the electronic device on which the program is executed to input information pertaining to status of the user,
- record information pertaining to performed transcranial brain stimulation of the user,
- correlate the information pertaining to status of the user and the information pertaining to performed transcranial brain stimulation of the user before being sent to the server, and
- send the correlated information to the server;

wherein the headset comprises:
- a wireless transceiver configured to wirelessly communicate with the electronic device,
- a circuit comprising a first electrode, a second electrode and a power source configured to provide power to the circuit, and
- a controller being configured to control powering of the circuit according to the control signal.

4. The system according to claim 3, wherein prompt the user of the electronic device on which the program is executed to input information pertaining to status of the user comprises prompt the user of the kit to input information pertaining to status of the user according to Phq-9, Hamilton Rating Scale for Depression (HRSD), Beck Depression Inventory (BDI, BDI-1A, BDI-II), Montgomery Asberg Depression Rating Scale (MADRS, MADRS-s), Young Mania Rating Scale (YMRS) or any other psychiatric rating scale.

* * * * *